United States Patent
Mallya et al.

(10) Patent No.: US 11,983,871 B2
(45) Date of Patent: May 14, 2024

(54) AUTOMATED SYSTEM FOR RAPID DETECTION AND INDEXING OF CRITICAL REGIONS IN NON-CONTRAST HEAD CT

(71) Applicant: KONINKLIJKE PHILIPS N.V., Eindhoven (NL)

(72) Inventors: Yogish Mallya, Bangalore (IN); Vidya Madapusi Srinivas Prasad, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 311 days.

(21) Appl. No.: 17/599,080

(22) PCT Filed: Mar. 24, 2020

(86) PCT No.: PCT/EP2020/058066
§ 371 (c)(1),
(2) Date: Sep. 28, 2021

(87) PCT Pub. No.: WO2020/200901
PCT Pub. Date: Oct. 8, 2020

(65) Prior Publication Data
US 2022/0172357 A1 Jun. 2, 2022

(30) Foreign Application Priority Data
Apr. 2, 2019 (IN) .............................. 201941013219

(51) Int. Cl.
*G06T 7/00* (2017.01)
(52) U.S. Cl.
CPC .. *G06T 7/0012* (2013.01); *G06T 2207/10081* (2013.01); *G06T 2207/20021* (2013.01);
(Continued)

(58) Field of Classification Search
CPC ............ G06T 2207/30004; G06T 7/20; G06T 2207/10104; G06T 7/0012; G06T 7/0016;
(Continued)

(56) References Cited

U.S. PATENT DOCUMENTS 9,165,360 B1   10/2015  Bates
2008/0317317 A1* 12/2008  Shekhar ................ G06T 3/0081
                                                            382/131
(Continued)

FOREIGN PATENT DOCUMENTS

WO    WO2019051271 A1    3/2019

OTHER PUBLICATIONS

PCT International Search Report, International application No. PCT/EP2020/058066, dated Jul. 6, 2020.
(Continued)

*Primary Examiner* — Ajibola A Akinyemi
(74) *Attorney, Agent, or Firm* — Larry Liberchuk

(57) ABSTRACT

The invention relates to a processing system and corresponding method for processing image data and for indexing regions of interest in an object of interest. The system comprises a registration unit for registering the image data, a sub-volume generator generating sub-volumes from the image data, a composite image generator for generating multiple sets of composite images from each sub-volume, each set of composite images representing a different projection. The system comprises an indexing unit for generating indexed regions of interest in each sub-volume by assessing each of the set of composite images in parallel and a combining unit for combining each set of composite images of each sub-volume into a scan level prioritization.

14 Claims, 12 Drawing Sheets

(52) U.S. Cl.
CPC ............... *G06T 2207/20084* (2013.01); *G06T 2207/30016* (2013.01)

(58) Field of Classification Search
CPC . G06T 2207/10081; G06T 2207/10108; G06T 5/50; G06T 2207/10088; G06T 2207/10101; G06T 2207/30041; G06T 7/0014; G06T 7/30; G06T 11/005; G06T 19/006; G06T 2207/10016; G06T 2207/10048; G06T 2207/10116; G06T 2207/20081; G06T 2207/20221
USPC .......................................................... 382/128
See application file for complete search history.

(56) References Cited

U.S. PATENT DOCUMENTS

| | | | |
|---|---|---|---|
| 2010/0027861 A1* | 2/2010 | Shekhar | G06V 10/755 382/128 |
| 2010/0183211 A1 | 7/2010 | Meetz | |
| 2012/0184840 A1 | 7/2012 | Najarian | |
| 2013/0094737 A1 | 4/2013 | Kelly | |
| 2016/0027184 A1* | 1/2016 | Courtney | G06T 15/08 345/424 |
| 2018/0070917 A1* | 3/2018 | Rothberg | A61B 8/4472 |
| 2018/0082443 A1 | 3/2018 | Risman | |
| 2018/0365824 A1 | 12/2018 | Yuh | |
| 2018/0365828 A1 | 12/2018 | Mansi | |
| 2019/0021677 A1 | 1/2019 | Grbic | |

OTHER PUBLICATIONS

Arbabsi Hirani M. R. et al., "Advanced Machine Learning in Action: Identification of Intracranial Hemorrhage on Computed Tomography Scans of the Head with Clinical Workflow Integration", NPJ Digital Medicine, vol. 1. No. 1., Apr. 4, 2018, XP055698337.

Qashqari K. A. et al., "Accuracy of Non-Contrast CT Brain Interpretation by Emergency Physicians: A Cohort Study", Pakistan Journal of Medical Sciences, vol. 29, No. 2, pp. 549-553, 2013.

Khoo N.C. et al., "Out of Hours' Non-Contrast Head CT Scan Interpretation by Senior Emergency Department Medical Staff", Emergency Medicine Australasia, 19.2 (2007): 122-128.

Iandola F. et al, "Densenet: Implementing Efficient ConvNet Descriptor Pyramids", 404.1869 (2014).

He, K. et al., "Deep Residual Learning for Image Recognition," 2016 IEEE Conference on Computer Vision and Pattern Recognition, (CVPR), pp. 770-778, Jun. 2016.

Otsu N. et al., "A Threshold Selection Method from Gray-Level Histograms", IEEE Transactions on Systems, Man, and Cybernetics, vol. smc-9. No. 1, pp. 62-66, Jan. 1979.

Chang P. D. et al., "Hybrid 3D/2D Convolutional Neural Network for Hemorrhage Evaluation on Head CT." American Journal of Neuroradiology 39.9 (2018): 1609-1616.

Chilamkurthy S. et al., "Deep Learning Algorithms for Detection of Critical Findings in Head CT Scans: A Retrospective Study", The Lancet, vol. 392, iss. 10162, Dec. 2018, pp. 2388-2396.

Desai V. et al., "Application of Deep Learning in Neuroradiology: Automated Detection of Basal Ganglia Hemorrhage using 2D-Convolutional Neural Networks", 2017, Computer Vision and Pattern Recognition (cs.CV).

Liu R. et al., "Hemorrhage Slices Detection in Brain CT Images", 19th International Conference on Pattern Recognition (ICPR 2008), Tampa, Florida, USA, Computers & Artificial Intelligence Machine Learning in Radiology, Dec. 2008.

Wang H-C. et al., "A Simple, Fast and Fully Automated Approach for Midline Shift Measurement on Brain Computed Tomography", 2017, Medical Physics (physics.med-ph); Computer Vision and Pattern Recognition.

\* cited by examiner

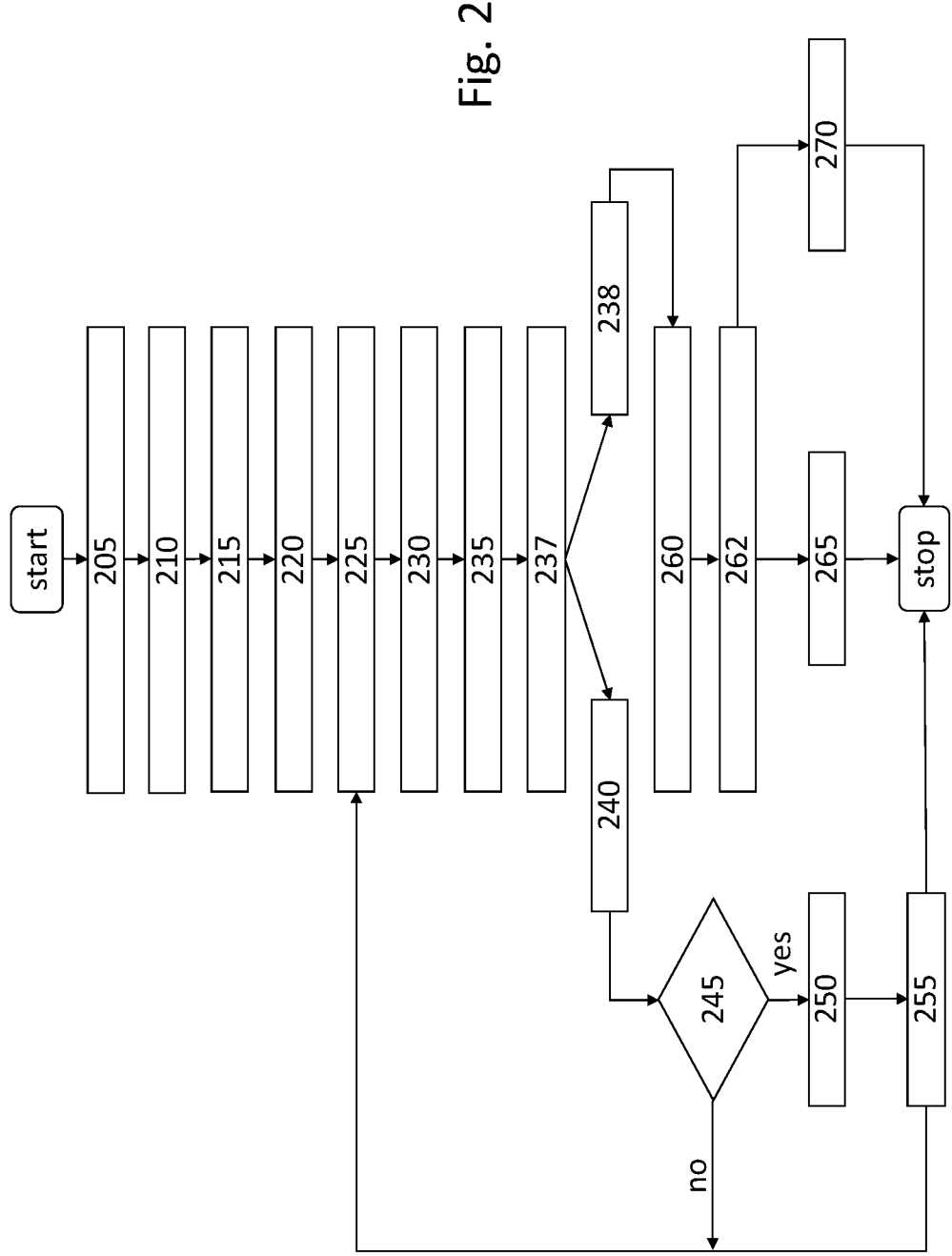

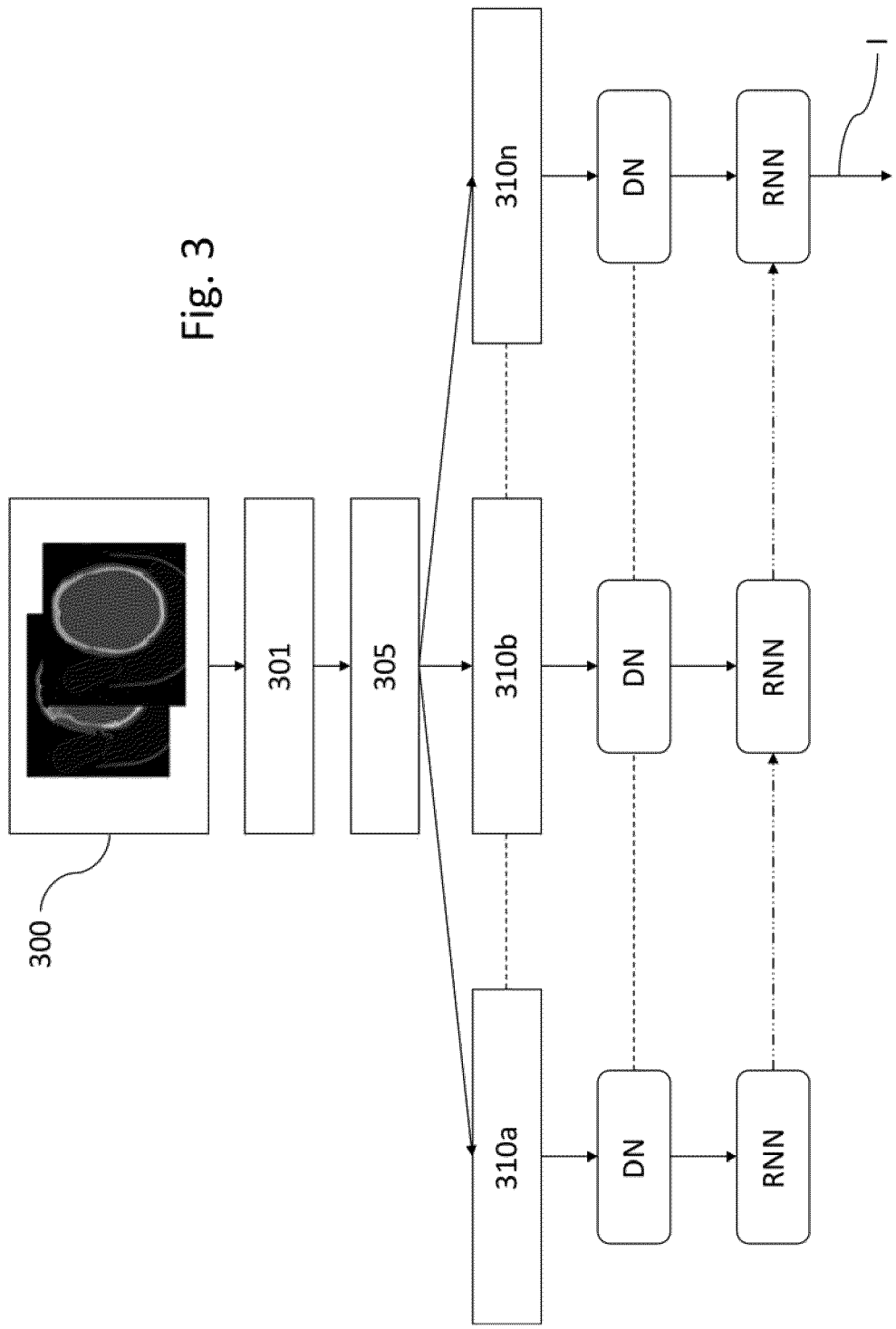

Fig. 5a    Fig. 5b
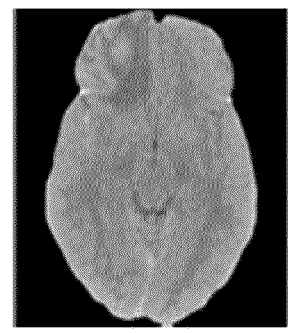
Fig. 6a    Fig. 6b
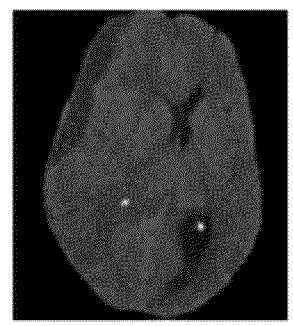
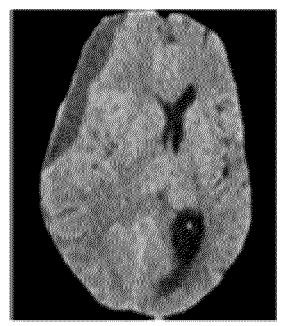
Fig. 7a    Fig. 7b

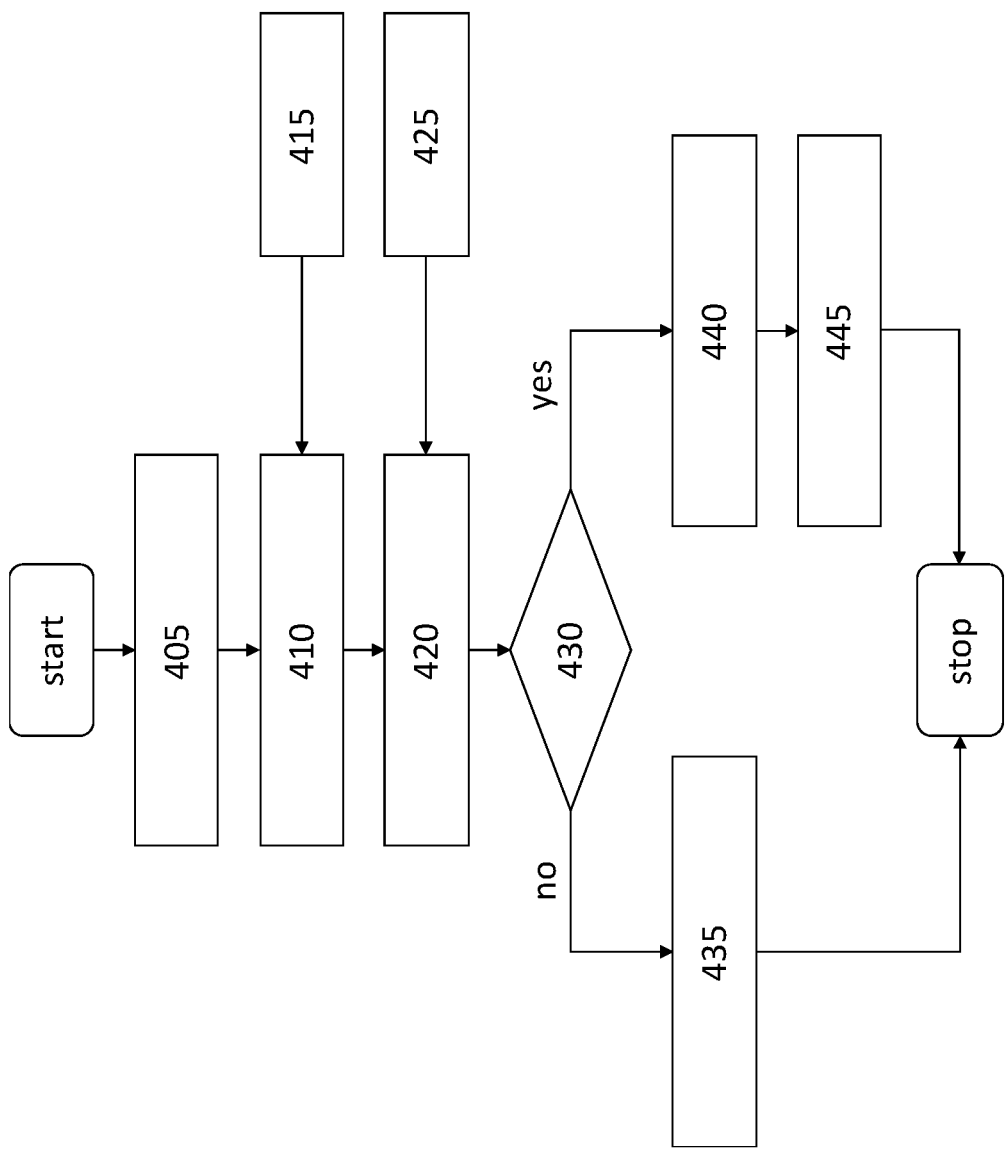

US 11,983,871 B2

AUTOMATED SYSTEM FOR RAPID DETECTION AND INDEXING OF CRITICAL REGIONS IN NON-CONTRAST HEAD CT

TECHNICAL FIELD

The present invention relates generally to a processing system for processing image data of an object of interest and for indexing regions of interest in the object of interest and a method for processing image data of the object of interest and indexing regions of interest in the object of interest.

BACKGROUND OF THE INVENTION

Non-contrast Head CT (NCHCT) imaging is a non-invasive and frequent radiological scan of a head (object of interest) of a patient, being used for screening in emergency departments for examination of neurological neurologic and traumatic complaints, in both critical and non-critical cases. They are widely available and have relatively low acquisition time, which make them the imaging modality of choice in patients visiting any emergency service and could be the only investigation to guide management in patients with head trauma or stroke symptom.

The diagnosis obtained from CT images determines the subsequent treatment path. In critical cases, such as trauma, time to treatment is of utmost importance and the physician must determine the subsequent treatment at the earliest.

With the increasing accessibility of CT scanning (imaging) there is a growing problem in areas where a trained radiologist may not be available for interpretation. Also, during the 'out-of-hours' period, senior emergency department medical staff are only correct two-thirds of the time in interpretation, hence still relying on a radiologist for final decision.

Given, the volume of patients needing CT coming into an emergency department, an immediate preliminary radiology reports to trigger appropriate level of care is paramount in an emergency department. There is an immediate critical need for a preliminary triaging (or indexing) system to detect life threatening pathologies for prioritization and also pre-identification of the effected region (regions of interest), hence expediting the diagnosis & treatment process and improving patient care.

Currently, deep convolutional neural networks (DCNNs) have become the dominant machine learning approach for medical image classification tasks. The data-driven nature of DCNNs benefits from the increasing volume of publicly accessible medical imaging datasets. Existing literature uses state-of-the-art DCNNs like Dense Convolutional Network (DenseNet) models and Residual Network (ResNets) models. Both these models are being transfer learned for medical image classification.

Current solutions in the automated interpretation of non-contrast head CT, focus on 3-dimensional (3D) whole scan analysis. A 3D whole scan model considers contextual information, while making its predictions. However, while assessing large scans, small regions of bleeds can be easily missed on consecutive pooling as in DCNNs.

Some anomalies are also dependent on inter-slice contextual information (such as a mass effect indicated by a vertical push of the ventricles), and a model built at a slice level will not be able to detect these unless the model is also provided with contextual information. A slice level analysis although good at identification of small anomalies (e.g. minute regions of bleed), could be compute and time intensive. It is also an extremely time consuming and expensive process for an expert to label each slice required for the training of these models.

There is a need for an improved indexing of regions of interest in an object of interest that is faster, less complex and takes into account contextual information as well as well as addressing the problem of missing small-sized anomalies.

SUMMARY OF THE INVENTION

It is an object of the invention to provide a system and a method for processing image data of an object of interest that solves above-mentioned problems or at least provide an alternative.

In particularly, it is an object of the invention to provide a system and a method that provides a faster indexing or anomaly prioritization taking into account contextual information in the image data as well as small-sized anomalies in the object of interest.

In a first aspect of the present invention a processing system for processing image data of an object of interest and for indexing regions of interest in the object of interest is provided.

The image data typically is generated by an imaging system such as a CT imaging system, particularly a non-contrast head CT imaging system. In case of a non-contrast head CT imaging system, the object of interest is a head of a patient.

The processing system comprises a registration unit configured for registering the image data from an imaging system.

The image data is generated by the CT imaging system and received and registered by the processing system. The image data may be 3D volume image data representing the object of interest, for example a head of patient. In an embodiment, the image data is received by a segmenting unit or extraction unit that extracts regions of interest such as brain and skull region extraction.

The processing system further comprises a sub-volume generator configured for generating sub-volumes from the image data, each sub-volume having a slab thickness. Each slab thickness comprises several slices of the original scan. Preferably, the sub-volumes are created from the axial view of the original image data or scan data. Alternatively, the sub-volumes are created from the coronal view of the original image data or scan data. In a most preferred embodiment, the sub-volumes are created from the axial view and the coronal view of the original image data or scan data.

The processing system is configured for generating sub-volumes from the received and registered image data, which typically is 3D volume image data. By creating sub-volumes, the 3D volume image data is divided into multiple sub-volumes each having a slab thickness. Preferably, the registered image data or 3D volume image data is divided such that the sub-volumes have an optimal slab thickness, ensuring that small anomalies are covered.

The processing system also comprises a composite image generator configured for generating multiple sets of composite images from each sub-volume, each set of composite images representing a different projection. Preferably, each composite image is a 2-dimensional (2D) composite image. In other words, multiple 2-dimensional (2D) composite images of sub-volumes are created from the original scan.

By generating multiple sets of composite images from each sub-volume the risk of losing critical information in the image data is reduced, making it more robust. It allows a better visibility for a myriad of anomalies. Therefore, the composite image generator creates multiple composite images for a single sub-volume. Preferably, there are three different types of composite images, being a maximum intensity projection (MIP), a minimum intensity projection (MinIP) and a projection based on a threshold selection from gray-level histograms (OtsuIP).

The projection based on a threshold selection from gray-level histograms is preferable the projection method as published by Nobuyuki Otsu with the title "*A Threshold Selection Method from Gray-Level Histograms*", IEEE Transactions on systems, man, and cybernetics, vol. smc-9. No. 1, January 1979, hereby incorporated by reference.

Having a set of composite images based on the MIP has as advantage that hyper-dense regions (such as bleeds) are preserved.

Having a set of composite images based on the MinIP has as advantage the hypo-dense regions, ventricles and subdural anomalies are preserved.

Having a set of composite images based on OtsuIP further reduces the risk of suppression of relevant information because it takes into account the maximum variance point across combined slices.

The processing system comprises an indexing unit configured for generating indexed regions of interest in each sub-volume by assessing each of the set of composite images in parallel.

Preferably, the sub-volumes are created from the axial view and the coronal view. This results in axial view sub-volumes and coronal view sub-volumes. This allows assessment of coronal plane slices to detect vertical pull/push of brain structures. State of art systems for detecting anomalies in the head using CT focus only on the assessment of the axial scan or axial view. This was done slice wise and without the context of the surrounding few slices. Considering the coronal view sub-volumes allows detecting clinical conditions that are more complex, such as the mass effect. For this, it is beneficial to assess the coronal view as this condition may manifest in the vertical movement of structures. The limitations of slice wise assessment are overcome by also taking into consideration the contextual information in the vertical direction by assessment of the coronal view, which is important in detection of vertical push/pull of structures which could look otherwise normal if only the axial view is considered.

The indexing unit preferably is a classifier configured for classifying anomalies in the object of interest and generating an anomaly probability score for each indexed region, the classifier preferably being a deep convolutional neural network (DCNN).

The processing system also comprises a combining unit configured for combining each set of composite images of each sub-volume into a scan level prioritization.

Preferably, the combining unit is configured to cascade each deep convolutional neural network of each set of composite images of each sub-volume (all sub-volumes) with a recurrent neural network thereby providing the scan level prioritization.

The advantage of cascading multiple DCNNs with a Recurrent Neural Network (RNN) is that it allows for consideration of contextual information across the sub-volumes.

As discussed earlier, for detecting complex clinical conditions such as mass effect, it is important to assess contextual information across slices. It is also important to assess contextual information in case of doubtful cases for clear demarcations (e.g. borders of calcifications across vertical slices). Automation of the same may be improved by cascading the sub-volume DCNN module with a recurrent based network.

Prioritization and pre-indexing may allow for a more efficient diagnosis.

The detected critical findings in the sub-volumes may be easily combined by using RNNs. This creates a patient level score or scan level prioritization and may be used for alerting and prioritization for immediate action.

In order to further improve the time to diagnosis and treatment, the invention also provisions pre-indexing of sub-volumes for each scan where critical pathologies are detected for immediate access when the scan is brought up for interpretation.

In other word, the invention comprises creating sub-volumes (of sufficient thickness) from the axial along with coronal view of the original scan (image data from the imaging system). Multiple composite images are generated from each sub-volume, using a maximum intensity projection (MIP), a minimum intensity projection (MinIP) and a projection generated from Otsu threshold points (OtsuIP). The three composite images of each-sub volume are then parallelly assessed for the detection of a critical pathology in the patient, and then combined to obtain a scan level prioritization. In cases where a critical finding is detected, an auto-selection of the effected sub-volume is performed, allowing an expert to immediately look at the critical region, hence improving time to diagnosis and treatment.

The inventions also relates to a method for processing image data of an object of interest and for indexing regions of interest in the object of interest. The method comprises the steps of:
  registering the image data from an imaging system by means of a registration unit;
  generating sub-volumes from the image data by means of a sub-volume generator, each sub-volume having a slab thickness;
  generating multiple sets of composite images from each sub-volume by means of a composite image generator, each set of composite images representing a different projection;
  indexing regions of interest in each sub-volume by means of an indexing unit by assessing each of the set of composite images in parallel; and
  combining the indexed regions of interest of each set of composite images into a scan level prioritization by means of a combining unit.

In an embodiment the method also comprises the step of brain/bone region extraction as explained further below. Preferably, this step is performed between the registering of the image data and the generation of the sub-volumes.

Preferably, the step of generating sub-volumes comprises the steps of creating sub-volumes from an axial view and creating sub-volumes from a coronal view.

Preferably, the step of generating multiple sets of composite images further comprises the steps of generating a set of composite images generated by means of a maximum intensity projection and generating a set of composite images generated by means of a minimum intensity projection and generating a set of composite images generated by means of gray-level thresh holding.

In an embodiment of the method according to the invention, the step of indexing further comprises classifying anomalies in the object of interest and generating an anomaly probability score for each indexed region by means of a classifier, the classifier preferably being a deep convolutional neural network (DCNN).

In a further embodiment of the method according to the invention, the step of combining further comprises cascading each deep convolutional neural network of each set of composite images of each sub-volume with a recurrent neural network thereby providing the scan level prioritization.

In an embodiment of the method according to the invention, the step of combining further comprises pre-indexing of the sub-volumes dependent on the scan level prioritization.

In other words, the method comprises one or more of the steps of:
- splitting each view (coronal and axial) into sub-volumes of desired thickness;
- creating composite images (MIP, MinIP, OtsuIP) from each sub-volume;
- assessing in parallel each set of composite images for a single sub-volume to detect critical findings;
- utilizing sub-volume predictions for pre-indexing and immediate access while viewing;
- creating view level predictions using contextual information across sub-volumes via an RNN;
- combining view level scores to create a patient level prediction;
- using patient level predictions to update a worklist and for prioritization.

In other words, time and computation complexity may be reduced, because assessment of the scan sub-volume wise (by creating composite images from each) rather than scan wise is more efficient in terms of time and computation complexity.

In critical cases, such as trauma, time to treatment is of utmost importance and the physician must determine the subsequent treatment at the earliest. Accurate initial assessment of the pathologies is required as this determines the case handler and treatment path (i.e. surgical or medical intervention) and any errors cause delays in time-to-treatment where NCHCT is sufficient.

BRIEF DESCRIPTION OF THE DRAWINGS

The present invention is now described by way of example with reference to the accompanying drawings in which:

FIG. 2 shows a schematic flow diagram of a method according to the invention;

FIG. 3 shows schematic flow diagram of a preferred method according to the invention;

FIGS. 5a and 5b show respectively a composite image generated by means of maximum intensity projection and minimum intensity projection of an axial scan/view containing hemorrhage with hydrocephalus;

FIGS. 6a and 6b show respectively a composite image generated by means of maximum intensity projection and minimum intensity projection of an axial scan/view containing hemorrhage within a hypo-dense region;

FIGS. 7a and 7b show respectively a composite image generated by means of maximum intensity projection and minimum intensity projection of an axial scan/view containing subdural hemorrhage;

FIG. 10 shows a schematic flow diagram of an embodiment of a method according to the invention;

The processing system is an automated system for rapid detection and indexing of critical regions to improve time to diagnosis and treatment. FIG. 1 shows how the invention fits into a workflow in a hospital. Digital images S1, S2, ... Sn or image data A is captured or scanned from various scanners or image acquisition units 110. The image data A is first checked for quality and standardized by means of a quality and standardization unit 120.

Figure 1:
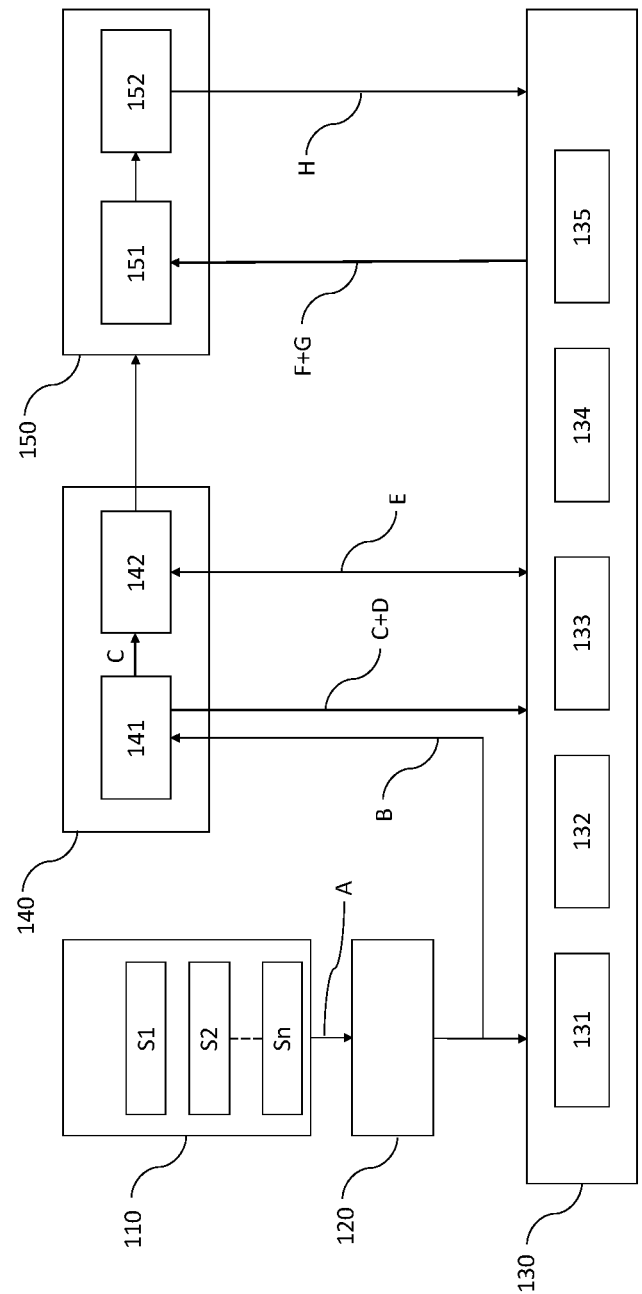
FIG. 1 shows a processing system according to the invention, together with an imaging system and an imaging review system.

The verified digital image B is then stored in an image storage server 131, and also passed to the processing system 140 being an assessment and assignment unit. The processing unit 140 comprises a scan review unit 141 that comprises a sub-volume generator, a composite image generator, an indexing unit and a combining unit.

The scan review unit 141 may also comprise a registration unit 130. Alternatively, the registration unit is the image storage server 131. Once the verified image data B is received at the scan review unit 141, it is processed, and a criticality score C and indexed slices of interest D are found from each of the sub-volumes and stored back in a reviewed image storage server 132 therefore comprising an archive of reviewed images.

In parallel, the criticality score C for the reviewed images are passed to a workload assignment unit 142, within which a worklist E may be updated by referring to the criticality scores C and stored back to a worklist storage server 133. Finally, at a viewing and reporting unit 150, the worklist E is retrieved for the individual from a configuration storage server 134.

When a user at an intelligent viewing station 151, queries an image in the worklist C, the system also retrieves pre-indexed slices of interest G identified by the processing system 140 or scan review unit 141, and displays the same through display 152. The user can then create reports H and may diagnose the case, which finally goes back into a report storage server 135.

The scan review unit 141 or image review unit, comprises the sub-volume generator, the composite image generator, the indexing unit and the combining unit.

The sub-volume generator generates sub-volumes from the verified image data B, wherein each sub-volume having a slab thickness.

The composite image generates multiple sets of composite images from each sub-volume wherein each set of composite images representing a different projection.

The indexing unit generates indexed regions of interest in each sub-volume by assessing each of the set of composite images in parallel.

The combining unit combines the indexed regions of interest of each set of composite images into a scan level prioritization.

FIG. 2 shows a schematic flowchart of the image/scan review unit 141.

In a first step 205, an input scan or verified image data B is retrieved 205 from the verified image storage server 131.

In a separation and enhancement step 210, the scan is separated/segmented/extracted into brain and skull regions after application of brain and bone windowing for the enhancement of contrast.

The flowchart represents analysis of the brain region only, a similar approach is followed for the skull.

In an example, intracranial regions in a head are extracted using an unsupervised method. This comprises two major steps, first the identification of a region of interest ROI and the slice containing the largest brain region and the second step is the fine extraction of the brain region.

The ROI and slice containing the largest brain region are identified as follows by means of the following sub-steps:
applying a brain windowing on the original scan;
dividing the brain into three regions, bone, air, and soft tissue using intensity values of the brain-windowed scan S;
identifying for each slice the largest bone island;
fitting a convex hull on the largest bone island (represents the region of interest for the slice);
creating an ROI mask Rmask and a masked brain scan R using the hull identified for each slice;
identify, in parallel, the slice containing the largest brain region, by finding the largest soft tissue island $C_{Ri}$ for each slice $R_i$ from R, wherein the slice index containing the largest area of this soft tissue contour is given by, $$\text{slice}_{maxbr} = \text{argmax}_i(\text{area}(C_{Ri})), \forall R_i \in R \quad (1)$$

From the ROI scan R, and largest brain volume slice ($\text{slice}_{maxbr}$) the brain region B is extracted by means of the following sub steps:
for the slice $R_i$ where i=$\text{slice}_{maxbr}$, identifying the brain region ($\text{Bmask}_i$) by the largest soft tissue contour in the slice;
for each slice Ri where i>$\text{slice}_{maxbr}$, first multiplying the slice with the mask of the previous slice $\text{Bmask}_{i-1}$ to obtain, a filtered slice $RF_i$;
creating a brain region mask using a maximum of three largest contours identified above;
removing contours smaller than a threshold T, applying an opening filter to further remove noise and applying a simple region growing in order to create a slice level brain region mask $\text{Bmask}_i$;
for each slice $R_i$ where i<$\text{slice}_{maxbr}$, first multiplying the slice with the mask of the next slice $\text{Bmask}_{i+1}$ to obtain a filtered slice $RF_i$. Follow steps 3-4;
Finally, multiplying the ROI scan R with $\text{Bmask}_i$ to obtain the brain region extracted scan B.

Figure 12:
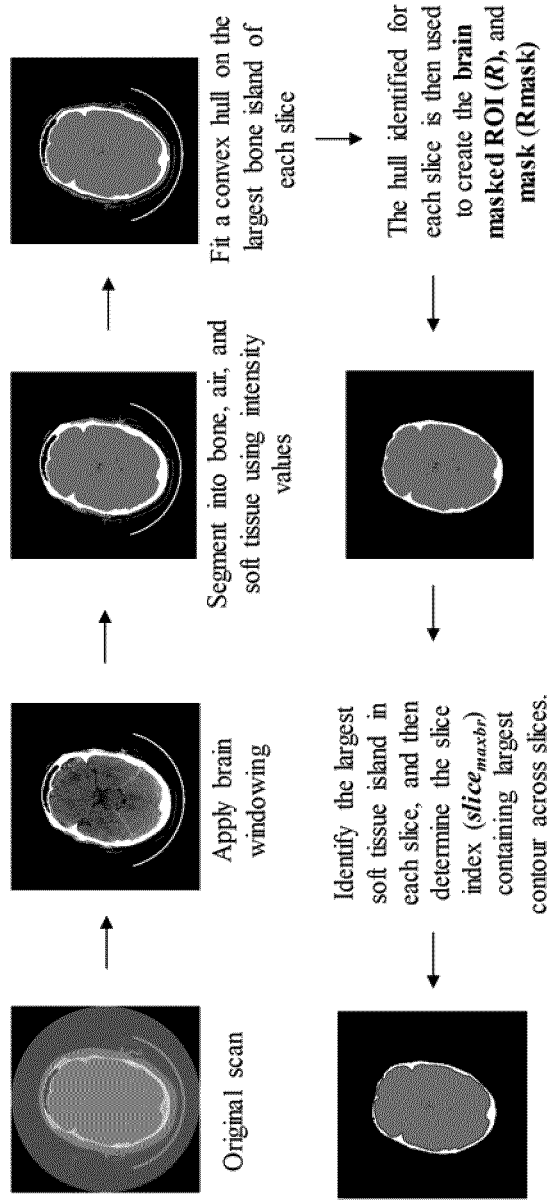
FIG. 12 shows an overview of brain ROI extraction and identification of a largest brain area slice ($slice_{maxbr}$)
Figure 13:
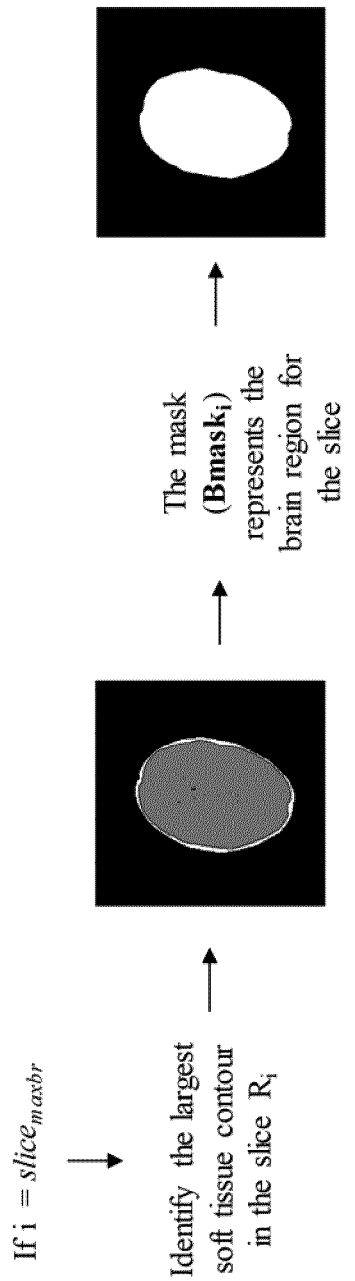
FIG. 13 shows a fine extraction of the brain region when slice i=$slice_{maxbr}$.
Figure 14:
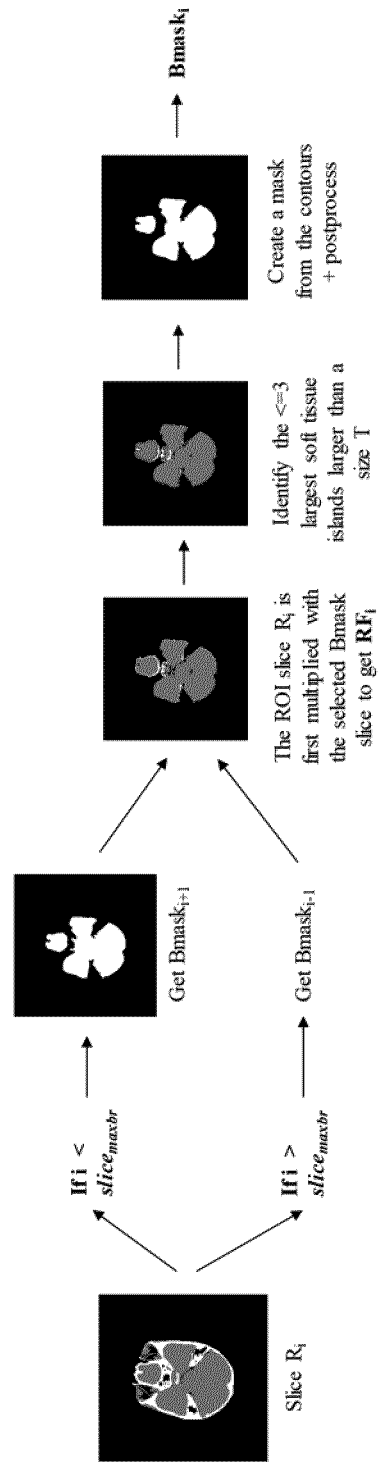
FIG. 14 shows a fine extraction of the brain region when slice i<$slice_{maxbr}$ or i>$slice_{maxbr}$.

In FIGS. 12, 13 and 14 the steps of respectively brain ROI extraction and identification of a largest brain slice, fine extraction of the brain region when slice i=$\text{slice}_{maxbr}$, and fine extraction of the brain region when slice i<$\text{slice}_{maxbr}$ or i>$\text{slice}_{maxbr}$ are disclosed in an overview.

From the brain region scans, the coronal and axial views are created from the original by reordering the pixel values appropriately. In other words, axial views and coronal views are created 215.

In a next step 220, each of the generated views are then split in n sub-volumes (for example 16) to give a total of 2n sub-volumes.

In a next step 225, for each sub-volume i, three composite images using MIP, MinIP and OtsuIP are generated.

Once the three composite images for the given sub-volume i are obtained, they are passed into the RGB channels respectively of a DCNN to be processed in parallel in a parallel processing step 230 for classification.

Preferably, a DenseNet-121 is used as a classifier for the detection of anomalies at a sub-volume level. Such a DenseNet-121 is disclosed by a publication from Iandola, F., Miskewicz, M., Karayev, S., Girshick, R., Darrell T., and KEutzer K, with the title "*Densenet: Implementing efficient convnet descriptor pyramids*", arXiv preprint arXiv: 1404.1869 (2014), which publication is hereby incorporated by reference.

In a next step 240, each composite image set is passed through the DCNN to get a probability score.

The probability score is defined by the following equation:

$$\tilde{p}_{iv}(a) = \frac{1}{1 + \exp(-p_{iv}(a))} \quad (2)$$

where i is the input composite images passed as a single RGB image of a given sub-volume, $\tilde{p}_{iv}(a)$ represents the probability score of the sub-volume image i, view v belonging to a critical class a.

In a checking step 245, it is checked whether the probability score is over a threshold T, in order to determine whether or not the sub-volume contains a critical pathology, thereby indexing it.

The threshold T can be configured. If the score is larger than T, then the index of the first and last slice of the sub-volume with respect to the full scan, the view type (i.e. coronal or axial), and the probability score is noted along with a scan ID and stored back in the image review archive. In other words, it comprises a step 250 of getting the index of the first and last slice in the sub-volume with respect to the full scan and a step 255 of saving indices, view type and probability scores to an image review archive.

In order to combine sub-volume scores to a scan level prediction and also to take into consideration the contextual information across the sub-volumes, the method comprises a step 238 of cascading the DCNN with a Recurrent Neural Network RNN.

Therefore, in a step 237, the output of the last global average pooling layer of the DCNN of each sub-volume I for a given view v is extracted to get a set of features f.

The feature set f of each of the n sub-volumes of a given view v is then fed into an RNN in a step 328 also shown in FIG. 3.

In an embodiment, the RNN consists of a single gated recurrent unit layer GRU, of input/output size 1024/2048 respectively. The GRU is followed by a fully connected layer of output size 1.

In a step 260, a last time-step output of the RNN is extracted and normalized using the sigmoid function for computation of a scan level anomaly probability scores $\tilde{p}_v$ similarly to Eq. 2. The scan level anomaly probability score is the scan level prioritization or a view level prioritization or a view criticality score.

Once all the v views are processed and scores are obtained, an overall patient level criticality score is obtained by taking the maximum of each of the view scores i.e. max($P_v, \forall v \in \{\text{axial, coronal}\}$), which is shown in a step 262.

In a storing step 265, this score is then stored back in the image review archive and is also sent to the workload assignment unit for prioritization.

FIG. 3 shows an overview of the method according to the invention. In a registering step 300, image data or an input view v or an input scan is acquired from an imaging system and registered by means of a registration unit.

In a preferred embodiment, a next windowing and extraction step 301 is performed.

In a next step 305, sub-volumes are generated from the image data by means of a sub-volume generator wherein each sub-volume has a slab thickness. Preferably, image data is divided into n sub-volumes ($i_1, i_2, \ldots, i_n$).

In subsequent steps 310a, 310b and 310n, multiple sets of composite images are generated from each sub-volume n by means of a composite image generator. Each set of composite images representing a different projection.

In step 310a said a set of composite images is generated for a first sub-volume. In step 310b said a set of composite images is generated for a second sub-volume. And in step 310n said set of composite images is generated for a n-th sub-volume.

After respectively each of steps 310a, 310b, 310n (hence in each sub-volume in parallel), an indexing of regions of interest is performed by means of an indexing unit. In other words, each set of composite images in each sub-volume are assessed in parallel. Preferably, the assessment is done by means of a deep convolutional neural network DCNN preferably comprising a DenseNet model DN.

Preferably, once the three composite images for the given sub-volume are obtained, they are passed into the RGB channels respectively of a DCNN to be processed in parallel for classification. In a preference, a DenseNet-121 is utilized as classifier for the detection of anomalies at a sub-volume level.

There are two main components, the extracting of features by means of a feature extractor and classifying by means of a classifier.

The step of extracting of features by means of a feature extractor comprises 4 dense blocks as defined in a publication from Iandola, F., Miskewicz, M., Karayev, S., Girshick, R., Darrell T., and KEutzer K, with the title "*Densenet: Implementing efficient convnet descriptor pyramids*", arXiv preprint arXiv:1404.1869 (2014), which publication is hereby incorporated by reference.

The 4 dense blocks are followed by a global average pooling layer. The outputs of the global average pooling layer are then flattened into a 1-D vector denoted by $DF_i$. The features $DF_i$ are then fed into the classifier, comprising of a fully connected FC layer and a sigmoid activation for classification.

The final sigmoid activation layer is added to the normalized output vector $p_d(a|i)$ of FC layer by, $$\widetilde{p_d}(a|i) = \frac{1}{1+\exp(-p_d(a|i))} \quad (3)$$

where i is the input sub-volume, $\widetilde{p_d}(a|i)$ represents the probability score of sub-volume i belonging to the ICH class a. The parameter $W_d$ of the global feature extractor is optimized by minimizing the binary cross-entropy BCE loss:

$$L(W_d) = -l_a \log(\widetilde{p_d}(a|i)) - (1-l_a)\log(1-\widetilde{p_d}(a|i)) \quad (4)$$

All indexed regions of interest of each set of composite images of each sub-volume are subsequently combined by means of a combining unit. Preferably, the combining unit is a recurrent neural network RNN which outputs a scan level prioritization I which for example is indicative of the probability whether there is an anomaly or not.

Therefore, in a preferred embodiment, in order to combine the sub-volume scores to a scan level prediction and also to take into consideration the contextual information across the sub-volumes, the DenseNet is cascaded with a Recurrent Neural Network RNN. The output of the last global average pooling layer of the DenseNet each sub-volume DFi is extracted. $DF_i, \forall i$ for a given scan I are then fed into a RNN.

In an embodiment, the RNN consists of a single gated recurrent unit layer GRU of input/output size 1024/2048 respectively. The GRU is followed by a fully connected layer of output size 1. The output of the last sequence step FC is considered for the prediction of scan-level ICH.

The final sigmoid activation layer is added to the normalized output vector $p_r(a|i)$ of FC layer similarly to Eq. 3. The weights $W_r$ of the RNN are then optimized by the BCE loss.

For each sub-volume i of shape (J, K, L), where i={1, 2 . . . 2n}, j={1 . . . J}, k={1 . . . K}, l={1 . . . L}, the three composite images using MIP, MinIP and OtsuIP are generated as follows, $$MIP(i_{jk}) = \max(i(J=j, K=k)) \quad (5)$$

$$MinIP(i_{jk}) = \min(i(J=j, K=k)) \quad (6)$$

$$OtsuIP(i_{jk}) = otsu(i(J=j, K=k)) \quad (7)$$

Here, MIP is a maximum intensity projection and MinIP is a minimum intensity projection.

Furthermore, otsu determines an intensity value that represents the maximum variance point in the reduction of a gray level image to a binary image. It is found that, using this threshold point allows for capturing the most important differentiator across the slices. The MIP image helps in identification of hyper-dense regions, particularly hemorrhages. The MIP image is also beneficial to differentiate between calcifications and intense regions of bleeds. Preferably, in this case the number of sub-volumes n=16 as this appears to be sufficient during labeling.

Figure 4A:
FIGS. 4a, 4b and 4c show an example of three consecutive slices of an axial scan/view
Figure 4B:
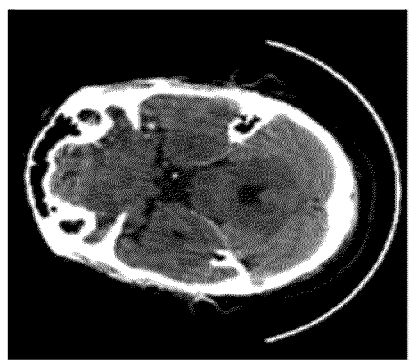
Figure 4C:
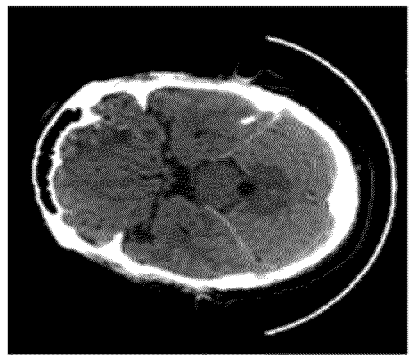
Figure 4D:
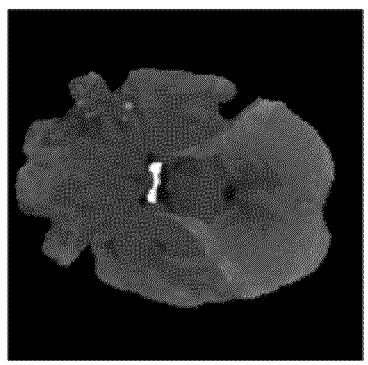
FIG. 4d shows a resulting composite image of said consecutive slices and FIG. 4e shows a full scan composite image.

As shown in FIGS. 4a, 4b, 4c and 4d MIP is efficient in capturing even extremely minute regions of hemorrhage. Here, FIGS. 4a, 4b and 4c show three consecutive slices of an axial scan or axial view with hemorrhage in a head of a patient. In other words, the object of interest is a head and a region of interest is the hemorrhage in the head. FIG. 4d shows the MIP composite image from a set of axial slices including (but not limited to) the axial slices of FIGS. 4a, 4b and 4d from the same axial scan.

Figure 4E:
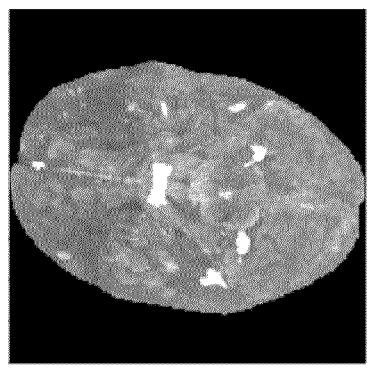

FIG. 4e shows a full scan MIP image for the same axial scan, where the hemorrhage is not visible.

The MinIP image allows for highlighting of abnormalities in ventricles, hypo-dense regions and abnormalities in the subdural region.

As shown in FIG. 5a, the MIP composite image helps in identifying the hemorrhage and as shown in FIG. 5b, the MinIP composite image shows a clear hydrocephalus.

Generally, the MinIP improves highlighting hypo-dense regions, making it easier to identify low-intensity bleeds, as shown in FIGS. 6a and 6d, and subdural hemorrhages as shown in FIGS. 7a and 7b.

FIGS. 6a and 6d respectively represent the MIP and MinIP of an axial scan containing hemorrhage within a hypo-dense region.

FIGS. 7a and 7b respectively represent the MIP and MinIP of an axial scan containing subdural hemorrhage.

Figure 8C:
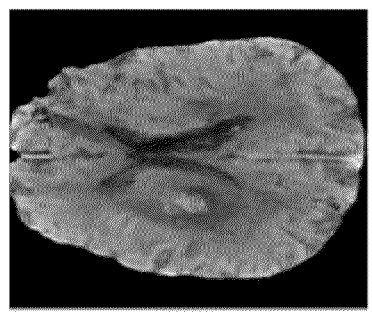
FIGS. 8a, 8b and 8c show composite images generated by respectively maximum intensity projection, minimum intensity projection and Otsu intensity projection of an axial scan/view containing hemorrhage with midline shift.
Figure 8B:
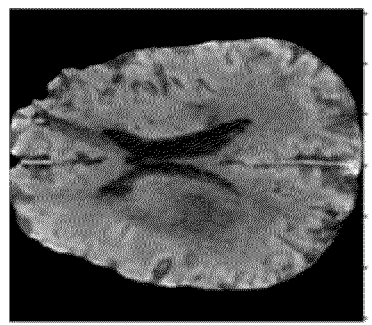
Figure 8A:
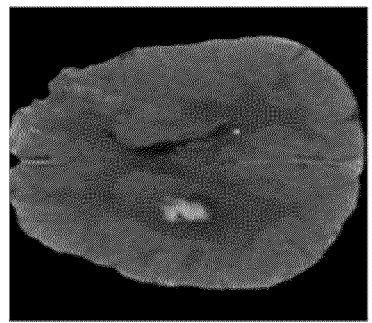

As shown in FIGS. 8a and 8b respectively MIP highlights a region of hemorrhage (region of interest) and MinIP highlights the effect on the ventricle (another region of interest). OtsuIP captures both the hyper-dense as well as hypo-dense regions very well as seen in FIG. 8c.

Figure 9B:
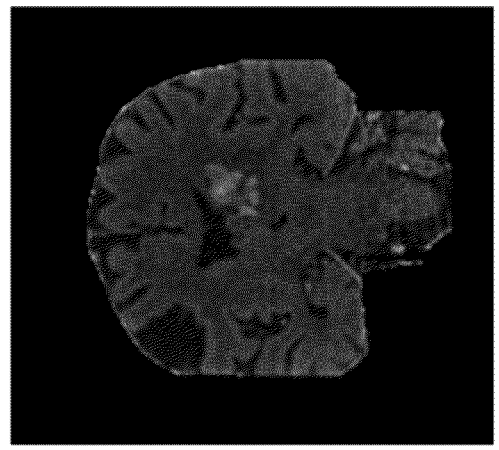
FIGS. 9a and 9b show respectively an axial scan/view and coronal scan/view of an object of interest containing hemorrhage with a mass effect.
Figure 9A:
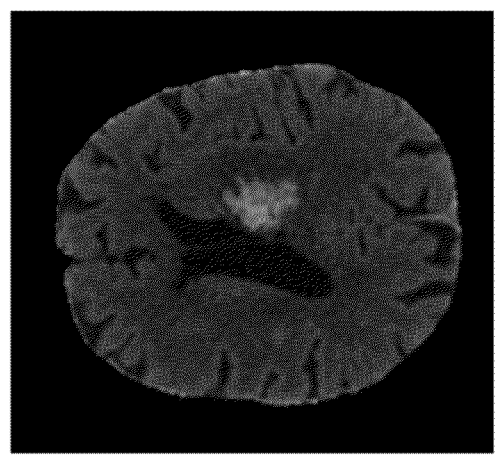

FIGS. 9a and 9b show a head of a patient with a hemorrhage resulting in a vertical push of the ventricles. This is clearly seen in the coronal view/scan of FIG. 9b, which can be easily detected using the composite image of the same. It is therefore beneficial to not only consider an axial scan/view such as shown in FIG. 9a but also the coronal view as it provides inter-slice contextual information for the axial slices.

An overall training procedure of the method as disclosed in FIG. 3 is presented below.

Apply the brain window, extract the brain region, obtain the MIP, MinIP and OtsuIP of the sub-volumes for each scan.

Train the DCNN (DenseNet) model on the sub-volume composite images using stochastic gradient descent optimizer (SGD) and the binary cross entropy loss (BCE) function to obtain $W_d$ weights of the network which outputs the normalized output probabilities of the individual sub-volumes.

Load the weights $W_d$ of the DenseNet model, and train he RNN for a further stage of fine-tuning ($W_r$ or $W_d$ along with $W_d$) using SGD optimizer on the BCE loss to obtain $W_r$ (and $W_d$) weights of the network which outputs the normalized output probabilities of each scan.

Below follows a more detailed description of an embodiment of the invention comprising a workload assignment unit.

Once the score i.e. criticality of a scan/view/image is generated by the (image) processing unit 140 it is then passed to a workload assignment unit 142.

The scan may then be classified based on the score into three zones, red (immediate attention), yellow (possible critical finding), and green (no urgent attention), based on pre-configured thresholds.

If a scan is in the red zone, an alert can be automatically made to the concerned expert for immediate action. The yellow zone scans are pushed to the front of the worklist following the red zone scans for prioritization. The green zone scans are not likely to have a critical finding but will still be assessed as per usual workflow in a hospital. The criticality type classification scores can be further used to assign a case handler (i.e. neurologist or neuro surgeon) with the priority scores for immediate assessment.

Figure 11:
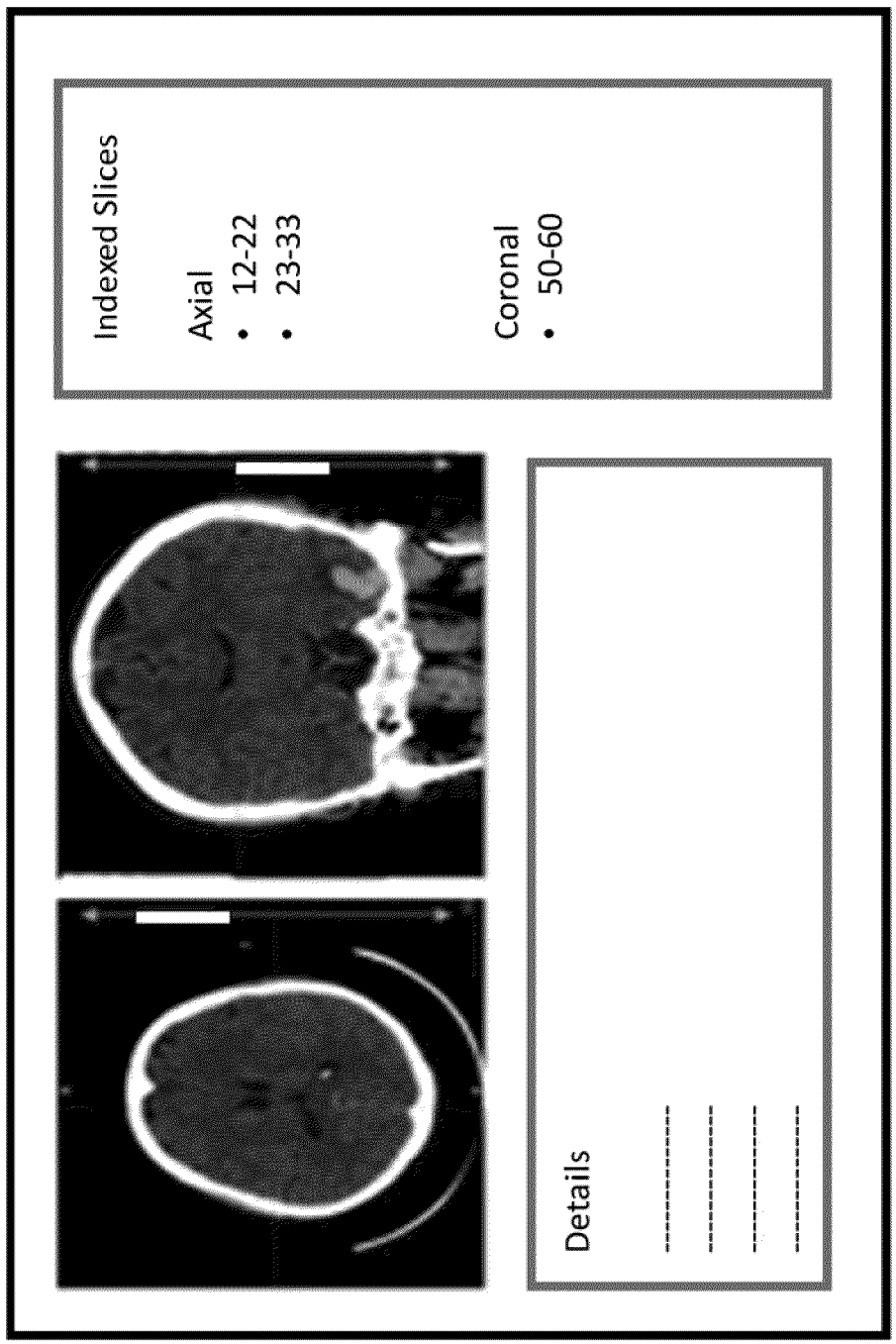
FIG. 11 shows a sample user interface of an image review system according to the invention.

As shown in FIGS. 10 and 11, the invention also includes an embodiment of viewing the pre-indexed slice (likely to have a critical pathology), during reporting and diagnosis by the radiologist/expert.

FIG. 10 shows a schematic flow diagram an embodiment of the method according to the invention comprising the step of pre-displaying of indexed slices.

At an intelligent viewing station (or display), the item at the top of a worklist is first retrieved 405. In other words, this step 405 is equivalent to getting an input scan/view.

The pre-indexed slices along with associated scores and view types are obtained 410 from an image review archive 415.

The configurations in the storage server are then checked to retrieve a pre-display flag 420, i.e. whether or not to preset the viewer to the specific slice(s) of interest.

If the pre-display flag is set to false, the default axial and coronal view of the scan is displayed 435. If the pre-display flag is set to true, then the indices associated with the largest sub-volume criticality score are identified 440. The viewer is then set such that the first slice of the sub-volume identified is in-view 445.

FIG. 11 shows a sample user interface of an intelligent viewing station (or display). Irrespective of the pre-display flag, the user can at any time view the regions of critical findings identified by the image review unit. By providing this, the user can assess the regions of interest and make a quick decision on the treatment path.

Summarized, the invention allows a fast and efficient system and method for the identification of critical findings in a non-contrast head CT, making it extremely useful in an emergency scenario, where quick action is needed.

The system and method can also be used in scenarios where there is an unavailability of radiologists as a second opinion to the physician.

In a validation study, a publicly available CQ500 dataset was used. This dataset contains a multitude of hemorrhage sub-types of various sizes. The study utilized a majority vote of the three radiologist labels to determine the ground truth. Sub-volume level labels were additionally created by an individual (having no clinical background or experience) for the training of the sub-volume DenseNet-121 network.

Rotation augmentations are applied to increase the dataset size by 12×. The train, test, validation split is 60, 20, 20 respectively for all our experiments with no overlap of patients. Each image is labeled with a 1 dimensional vector L=[$1_a$] in which $1_a \in 0,1$ where 1 represents the presence of ICH and 0 represents no ICH cases.

The results of the study showed an improvement by using sub-volumes and cascading a DCNN with an RNN.

In order to show the value of analyzing sub-volumes, a DenseNet model was trained (similarly as discussed earlier), on single MIP images obtained from the full scan and this was used as the baseline for our model (Full Scan MIP).

Further, another baseline was created by combining the sub-volume probabilities to obtain a scan level prediction using a simple maximum value operation (Sub-volume Max Score).

This allows presenting the value addition of using an RNN in the invention (Sub-volume RNN) to not only better learn the scan level ground truths, but also to handle the contextual aspects.

Table 1 below shows the comparison of the methods above. As seen, there is a significant improvement from a full scan analysis to sub-volume analysis because the small anomalies are better seen. There is also an improvement by combining the sub-volumes features with an RNN rather than using a simplistic maximum score. Table 2 shows a comparison of the invention with prior work.

TABLE 1 comparison of results of the various methods on the CQ500 test set. Specificity at a given high sensitivity control point is given.

| Method | AUROC | Sensitivity | Specificity |
| --- | --- | --- | --- |
| Full Scan MIP | 0.73 | 0.90 | 0.26 |
| Sub-volume Max Score | 0.89 | 0.90 | 0.60 |
| Sub-volume RNN | 0.91 | 0.90 | 0.79 |

TABLE 2

Comparison of proposed approach with prior work.
The metrics reported below Chilamkyurthy et. Al. are
on our test subset of the CQ500, where the TPR/TNR
(Sensitivity/Specificity) is taken at the point
where the difference is minimum.

| Method | AUROC | TPR/TNR | Train Data | Expert Label Type |
|---|---|---|---|---|
| Arbabshiranil et. al | 0.846 | 0.740/0.800 | 37074 scans | Scan Label |
| Chang et. al. | 0.975 | 0.971/0.975 | 10159 scans | Region annotation |
| Chilamkurthy et. al. | 0.929 | 0.842/0.851 | 4304 scans | Slice label |
| Sub-volume RNN | 0.914 | 0.842/0.830 | 295 scans | Scan label |

Arbabshirani, M. R., Fornwalt, B. K., Mongelluzzo, G. J., Suever, J. D., Geise, B. D., Patel, A. A., & Moore, G. J. (2018). Advanced machine learning in action: identification of intracranial hemorrhage on computed tomography scans of the head with clinical workflow integration. npj Digital Medicine, 1(1), 9.

Chang, P. D., Kuoy, E., Grinband, J., Weinberg, B. D., Thompson, M., Homo, R., Chen, J., Abcede, H., Sha_e, M., Sugrue, L. and Filippi, C. G., 2018. Hybrid 3D/2D convolutional neural network for hemorrhage evaluation on head CT. American Journal of Neuroradiology, 39(9), pp.1609-1616.

Chilamkurthy, S., Ghosh, R., Tanamala, S., Biviji, M., Campeau, N. G., Venugopal, V. K., . . . & Warier, P. (2018). Deep learning algorithms for detection of critical findings in head CT scans: a retrospective study. The Lancet, 392(10162), 2388-2396.

The RNN is generalized for any sequential data. The basic concept is that the RNN can store certain parameters from the previous states to compute values for the current state. In the invention, the 'state' refers to the current sub-volume being processed. The RNN is used to weight the parameters of the current sub-volume based on the previous sub-volume's information as well, which means it includes, the previous sub-volume context for decision making at a scan/view level. This improves the results.

The invention considers coronal along with axial, in order to assess the vertical pull/push of structures for mass effects. Although it appears that coronal is the best way to assess such vertical pull/push of structures for mass effect it is foreseen that any combination with a sagittal view may also be advantageous.

Summarized, the invention is an advantageous approach that combines the advantages of both slice level as well as whole scan analysis. Creating small sub-volumes ensures that it does not miss out minor anomalies and also allows increasing the dataset size and improve the learning. With the utilization of a RNN the contextual information across slices are also handled, which improves the results.

By creating multiple composite images to ensure that no important information is lost, the model is generalized to any anomaly in the brain region.

We claim:

1. A processing system for processing image data of an object of interest and for indexing regions of interest in the object of interest, the processing system comprising:
a registration unit configured for registering the image data from an imaging system;
a sub-volume generator configured for generating sub-volumes from the image data, each sub-volume having a slab thickness;
a composite image generator configured for generating multiple sets of composite images from each sub-volume, each set of composite images representing a different projection;
an indexing unit configured for generating indexed regions of interest in each sub-volume by assessing each of the set of composite images in parallel; and
a combining unit configured for combining each set of composite images of each sub-volume into a scan level prioritization.

2. The processing system according to claim 1, wherein the sub-volume generator is configured to create sub-volumes from an axial view and sub-volumes from a coronal view.

3. The processing system according to claim 1, wherein the multiple sets of composite images at least comprises:
a set of composite images generated by means of a maximum intensity projection;
a set of composite images generated by means of a minimum intensity projection; and
a set of composite images generated by means of gray-level thresh holding of a gray-level histogram.

4. The processing system according to claim 3, wherein the combining unit is configured to cascade each deep convolutional neural network of each set of composite images of each sub-volume with a recurrent neural network, thereby providing the scan level prioritization.

5. The processing system according to claim 1, wherein the indexing unit comprises a classifier configured for classifying anomalies in the object of interest and generating an anomaly probability score for each indexed region, the classifier being a deep convolutional neural network (DCNN).

6. The processing system according to claim 1, wherein the combining unit is further configured to pre-index the sub-volumes dependent on the scan level prioritization.

7. A CT imaging system, comprising:
an image acquisition unit for acquiring image data of the object of interest; and
a processing system according to claim 1.

8. An image review system, comprising:
a processing system according to claim 1; and
a display.

9. A method for processing image data of an object of interest and for indexing regions of interest in the object of interest, comprising:
registering the image data from an imaging system by a registration unit;
generating sub-volumes from the image data by a sub-volume generator, each sub-volume having a slab thickness;
generating multiple sets of composite images from each sub-volume by a composite image generator, each set of composite images representing a different projection;
indexing regions of interest in each sub-volume by an indexing unit by assessing each of the set of composite images in parallel; and
combining each set of composite images of each sub-volume into a scan level prioritization by a combining unit.

10. The method according to claim 9, further comprising:
creating sub-volumes from an axial view; and
creating sub-volumes from a coronal view.

11. The method according to claim 9, further comprising:
generating a set of composite images generated by a maximum intensity projection;
generating a set of composite images generated by a minimum intensity projection; and
generating a set of composite images generated by gray-level thresh holding.

12. The method according to claim 9, further comprising:
classifying anomalies in the object of interest and generating an anomaly probability score for each indexed region by a classifier, the classifier being a deep convolutional neural network (DCNN).

13. The method according to claim 9, further comprising:
cascading each deep convolutional neural network of each set of composite images of each sub-volume with a recurrent neural network, thereby providing the scan level prioritization.

14. The method according to claim 9, further comprising pre-indexing of the sub-volumes dependent on the scan level prioritization.

* * * * *